United States Patent
Wetta (10) Patent No.: US 11,157,808 B2
(45) Date of Patent: Oct. 26, 2021

(54) NEURAL NETWORK-BASED CONFIDENCE ASSESSMENT MODULE FOR HEALTHCARE CODING APPLICATIONS

(71) Applicant: 3M INNOVATIVE PROPERTIES COMPANY, St. Paul, MN (US)

(72) Inventor: Andrew C. Wetta, Chevy Chase, MD (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 1121 days.

(21) Appl. No.: 15/312,682

(22) PCT Filed: May 19, 2015

(86) PCT No.: PCT/US2015/031459
§ 371 (c)(1),
(2) Date: Nov. 21, 2016

(87) PCT Pub. No.: WO2015/179328
PCT Pub. Date: Nov. 26, 2015

(65) Prior Publication Data
US 2017/0185893 A1   Jun. 29, 2017

Related U.S. Application Data

(60) Provisional application No. 62/001,785, filed on May 22, 2014.

(51) Int. Cl.
| | | |
|---|---|---|
| *G06K 9/62* | (2006.01) | |
| *G05D 1/00* | (2006.01) | |
| *G06Q 50/30* | (2012.01) | |
| *G06N 3/08* | (2006.01) | |
| *G16H 40/20* | (2018.01) | |
| *G06F 19/00* | (2018.01) | |
| *G16H 10/60* | (2018.01) | |

(52) U.S. Cl.
CPC ............... *G06N 3/08* (2013.01); *G06F 19/00* (2013.01); *G06N 3/084* (2013.01); *G16H 10/60* (2018.01); *G16H 40/20* (2018.01)

(58) Field of Classification Search
CPC .......... G06N 3/08; G06N 3/084; G16H 40/20; G16H 10/60; G06F 19/00
USPC ....................................................... 706/1–62
See application file for complete search history.

(56) References Cited

U.S. PATENT DOCUMENTS

| | | | |
|---|---|---|---|
| 5,542,006 A | | 7/1996 | Shustorovich |
| 5,912,986 A | | 6/1999 | Shustorovich |
| 6,249,781 B1 | | 6/2001 | Sutton |
| 6,915,254 B1 | | 7/2005 | Heinze |
| 7,395,251 B2 | | 7/2008 | Linsker |
| 10,614,919 B1 * | | 4/2020 | Yedwab ................. G16H 50/20 |

(Continued)

OTHER PUBLICATIONS

3M[SM] CodeRyte[SM] CodeAssist[SM] System, 3M Health Information Systems, 2016, 2 pages.

(Continued)

*Primary Examiner* — Brandon S Cole
(74) *Attorney, Agent, or Firm* — Jonathan L. Tolstedt (57) ABSTRACT

A system including a confidence assessment module that implements a neural network to assess the likelihood that codes associated with a patient's encounter with a healthcare organization are accurate. The confidence assessment module may also be incrementally trained.

12 Claims, 4 Drawing Sheets

(56) References Cited

U.S. PATENT DOCUMENTS

| | | |
|---|---|---|
| 2004/0042650 A1 | 3/2004 | Ii |
| 2004/0199482 A1 | 10/2004 | Wilson |
| 2006/0112028 A1* | 5/2006 | Xiao ................. G06N 3/08 706/15 |
| 2007/0022068 A1 | 1/2007 | Linsker |
| 2007/0038622 A1* | 2/2007 | Meyerzon ............ G06F 16/951 |
| 2008/0004505 A1 | 1/2008 | Kapit |
| 2012/0065987 A1* | 3/2012 | Farooq ................ G06Q 10/109 705/2 |
| 2013/0161814 A1 | 6/2013 | Su |
| 2013/0339202 A1* | 12/2013 | Zhao ................... G06Q 30/04 705/34 |
| 2017/0185893 A1* | 6/2017 | Wetta ................... G06F 19/00 |

OTHER PUBLICATIONS

Bishop, Pattern Recognition and Machine Learning, 225-290, (2006).
Jiang et al. "How Does the System Know It's Right? Automated Confidence Assessment for Compliant Coding." Perspectives in Health Information Management, CAC Proceedings; Fall 2006, pp. 1-10.
Riedmiller, "A Direct Adaptive Method For Faster Backpropagation Learning: The RPROP Algorithm," IEEE International Conference on Neural Network, 1993, pp. 586-591.
Wetta, Accessing Note Confidence using Neural Networks, 3M Health Information Systems, Jan. 2013, pp. 1-7.
International Search Report for PCT International Application No. PCT/US2015/031459, dated Aug. 14, 2015, 2 pages.

\* cited by examiner

NEURAL NETWORK-BASED CONFIDENCE ASSESSMENT MODULE FOR HEALTHCARE CODING APPLICATIONS

CROSS REFERENCE TO RELATED APPLICATIONS

This application is a national stage filing under 35 U.S.C. 371 of PCT/US2015/031459, filed May 19, 2015, which claims the benefit of U.S. Provisional Application No. 62/001,785, filed May 22, 2014, the disclosure of which is incorporated by reference in its entirety herein.

BACKGROUND

Confidence Assessment Modules (CAMs), as used in a clinical coding context, are computer implemented modules that assess the probability that codes associated with a patient's encounter with a healthcare organization accurately reflect the patient's encounter. CAMs assess whether the codes are consistent with what a professional coder would assign. Such codes may be automatically generated, as described in Kapit et. al. (US Patent Publication No. 2008/0004505), through an analysis of encounter-related documentation. The codes may then be used to generate bills without further human review if, upon review by the CAM, there is a sufficiently high probability that the codes accurately reflect the patient's encounter with the healthcare organization. If the CAM determines an insufficient probability, then the encounter-related documentation may be queued up for human review, by a professional coder. The CAM, and the process of "training" the CAM by processing human-reviewed data using machine learning techniques is further described in Kapit. 3M Company, of St. Paul, Minn., has provided such CAM-related services through its CodeRyte℠ CodeAssist℠ software service offering.

SUMMARY

A confidence assessment module that evaluates coded encounters (comprising documentation associated with a patient's encounter with a healthcare organization, and associated codes) and calculates a confidence value indicative of the likelihood that the associated codes would be the ones chosen by a human coder, given the documentation. The confidence assessment module is implemented as a binary node-based neural network. In embodiments described herein, it is capable of incremental learning, meaning once it has been trained, it is possible to further refine the neural network model to properly evaluate new types of coded encounter correctly, based on a limited and specific corpus of training documents.

In one embodiment, a computer-implemented method of incrementally training a confidence assessment module that calculates a confidence value indicative of the extent to which a code associated with a patient's encounter with a healthcare organization is proper, the computer-implemented method is described, the method comprising assessing, with the confidence assessment module, a training corpus comprised of a plurality of coded encounters, to produce resultant confidence values associated with each encounter; comparing the resultant confidence values to a target confidence value; and, adjusting variables within the confidence assessment module to produce resultant confidence values closer to the target confidence value.

In another embodiment, an incremental learning confidence assessment system is described. The system evaluates coded encounters between a patient and a healthcare organization and computes a confidence value indicative of the likelihood that codes associated with the coded encounters are proper. The system comprises a confidence assessment module operative to receive coded encounters, the coded encounters comprising both (1) documentation associated with a patient's encounter with a healthcare organization, and (2) codes associated with that encounter, and using a neural network, compute the confidence value for the coded encounter; and, a training module that invokes the confidence assessment module to evaluate a corpus of training notes, then adjusts variables within the confidence assessment module based on the evaluation.

In yet another embodiment, a computer-implemented method of calculating a confidence value indicative of the likelihood that a code associated with a patient's encounter with a healthcare organization is proper is described. The computer-implemented method comprises analyzing, using a processor of the computer, patient-related healthcare records that relate to the patient's encounter with a healthcare organization, to extract attributes; representing at least some of the extracted attributes as binary input nodes associated with a neural network model that has an output node associated with the confidence value; and, applying the neural network model to the binary input nodes, to compute the confidence value associated with the output node.

These and other embodiments are further described herein.

DETAILED DESCRIPTION

A healthcare provider organization will, in the process of providing healthcare-related services to a visiting patient, generate a number of documents and data concerning the encounter. These health records as they will be referred to herein, contain information about the services rendered to the patient that are associated with an encounter, as well as other data concerning the patient, such as the patient's diagnosis, prognosis, demographics, etc.

After the encounter, the process by which the healthcare organization gets remuneration for the services rendered starts, typically, with the patient's encounter-related healthcare records, or documentation, being analyzed and represented as codes, which may then be submitted to a payment organization, such as an insurance company or the government. Such coding may be done manually, usually be trained personnel (often called coders) who manually review the patient's encounter-related healthcare records and determine relevant codes, or increasingly, such coding may be done by a computer system programmed to review the patient's encounter-related documentation and compute relevant codes.

For example, a patient's encounter-related documentation may include an attending doctor's dictation that describes the patient's condition and the services rendered to the patient. The encounter-related documentation may be processed to extract encounter-related features from the encounter-related documentation. Encounter-related features are portions, or snippets, of the encounter-related documentation determined to be of likely relevance to coding. For example, an attending doctor's dictation might be as follows:

"Xray finger. Three views of the left hand show no evidence of fracture or dislocation."

The encounter-related concepts that may be extracted from this dictation would include "xray", "finger", "3 views", "left", and "hand". "Finger" overrides "hand" because it is more specific in the exam title, and "fracture" and "dislocation" may be discarded because of the negated phrase "no evidence of." So the resulting features would be "xray", "finger", "3 views", and "left" which correspond to basic properties of a code like "procedure", "body part", and "laterality". These features may be automatically associated with a CPT diagnosis or procedure code of 73140-LT, which is "X-RAY EXAM OF FINGER(S)" with the "LT" modifier indicating left side.

Extraction of the constituent components of the dictation is common to many natural language processing (NLP) programs, and is well known in the art. Generally speaking, the process may involve extraction of metadata (such as the ordered exam title information (which may differ from what the doctor dictated), patient age and gender, and other relevant demographic data). Then various regions of the dictation may be identified, for example the exam title, clinical indication, and final impression sections. Next, known or likely medical vocabulary may be identified and tagged. The text may be parsed by one or more parsing algorithms to carry out syntactic analysis of the text to determine relationships among the identified vocabulary and clinical concepts, and to identify negated sections of the text, etc. The parser also assists in linking the clinical concepts to clinically relevant evidence.

The data set that includes the encounter-related features, (sometimes referred to as snippets—there could be multiple evidence snippets that are extracted: some for procedures, some for diagnoses, etc.) and the resulting codes is termed herein a "coded encounter." The codes being referred to may be any codes that are associated with the encounter-related features, but in the descriptions included herein they may be considered more narrowly billing-relevant codes, such as those provided by the International Classification of Diseases (ICD) published by the World Health Organization. Such codes are commonly referred to as either ICD-9 or 10 codes. Other sets of codes include the Current Procedural Terminology, or CPT, codes, provided by the American Medical Association. Auto-coded encounters are coded encounters wherein the codes have been generated automatically by a computer's analysis of the encounter-related features. Such auto-coders are known in the art; see for e.g. U.S. Pat. No. 6,915,254. In some embodiments, the encounter-related features are the same as the encounter-related documentation, but in usual practice the encounter-related features comprise some processed sub-set of the encounter-related documentation.

Auto-coded encounters, while very convenient for a healthcare organization, need to have assured quality (i.e., they need to be accurate) via some procedural mechanism. One such mechanism is the use of a confidence assessment module, or CAM. A CAM is used, for example, in healthcare analytics to assess whether auto-coded encounters may be sent "direct to bill", or instead are in need of review by, e.g., a human coder. Statistical-based non-incremental learning CAMs are used in the art, and generally consist of a statistics-based machine learning algorithm that is "trained" by exposing it to a number of training documents, or confirmed coded encounters, i.e., coded encounters that have been verified by a human coder. Statistical, non-incremental learning CAMs apply a model that is static and does not change after initial training, thus it assumes that the types of notes it evaluates are the same. This can lead to accuracy problems, including e.g., drift, whereby the coding practices of a healthcare organization change either suddenly (e.g., new group of doctors join, who do things a bit differently) or over time, resulting in decreased accuracy of the statistical CAM.

The precise number of coded encounters necessary to sufficiently train a statistical CAM using machine learning techniques may be dependent on a number of variables, such as the variability of the encounter-related documentation and the population of possible associated codes (to name just a couple). For a more complete discussion of the trade-off involved, see "How Does the System Know It's Right? Automated Confidence Assessment for Compliant Coding" by Yuankai Jiang, PhD; Michael Nossal, MA; and Philip Resnik, PhD. (http://library.ahima.org/xpedio/groups/public/documents/ahima/bok1_032075.pdf visited May 12, 2014).

In some instances it is thought that about 20,000 coded encounters is a sufficiently sized training data set that will produce a statistical CAM having adequate performance characteristics (foremost, accuracy). The process of training the statistical CAM, briefly, comprises presenting coded encounters to a machine learning algorithm, each coded encounter being characterized, or labeled, as "good" (meaning the codes would likely not be changed if audited by a professional coder) or "bad" (meaning the codes likely would be changed if audited by a professional coder). The characterization of "good" or "bad" may be inferred, when professional coders are involved in reviewing computer-generated codes, by comparing the degree to which the coder needed to modify a computer-suggested code base. If there were essentially no modifications, the coded encounter may be labeled "good"; if there were modifications, the coded encounter may be labeled "bad." The machine-based statistical learning algorithm may beneficially learn from both good and bad coded encounters. Though label attributes of "good" and "bad" are discussed herein, it is recognized that other label attributes could be employed.

Ideally, an initial training data set to first train a statistical CAM, i.e. 20,000 coded encounters, will have been reviewed (and corrected as needed) by a professional coder. Such review provides a high quality training data set for initially configuring the statistical CAM. Such a quality-assurance review assures high confidence that the coded encounters have codes that properly reflect the encounter-related documentation. An initially trained statistical CAM may provide years of service to an organization, reviewing coded encounters (usually auto-coded encounters) and determining a confidence level for each.

Auto-coded encounters associated with a high enough confidence level may be sent "direct-to-bill", that is, the codes may be provided to further billing systems to generate invoices that are submitted to payment organizations (usually insurers or the government), without professional coder review. In some implementations, 85% of auto-coded encounters (possibly even more) may be sent direct-to-bill based on the review of a statistical CAM. In most implementations, a percentage of auto-coded encounters sent direct-to-bill, for example, 2-5%, may be routinely reviewed by professional coders, as a quality control check. These coders may make no changes to the auto-coded encounter, or they may make changes. Additionally, all auto-coded encounters judged by the statistical CAM to be not direct-to-bill (i.e., CAM has lower confidence in them), are reviewed by professional coders.

From time to time, it may be advantageous to incrementally train a previously trained, and in many cases a production deployed, CAM. Some types of machine learning CAMs do not allow for such incremental training, and a new corpus of coded encounters must be assembled to train the statistical CAM from scratch (see, e.g., U.S. patent application Ser. No. 13/773,844, which describes a method of assembling a suitable training corpus from a subset of coded encounters.) Furthermore, the U.S. Department of Health and Human Services has mandated that ICD-10 codes be used starting in the Fall of 2015, instead of currently used ICD-9 codes. Because existing statistical CAMs have been trained on notes coded with ICD-9 codes, they will not be able to determine the confidence of notes coded with new ICD-10 diagnosis or ICD-10 procedure codes. The current statistical, non-incremental learning CAMs are static and are not able to adapt to the changes like this; they generally need to be completely retrained, which requires a corpus of documents, which may not be available, because it is difficult to acquire the needed number of coded encounters for retraining without drastically reducing the number of notes sent direct-to-bill. Thus a CAM that allows for incremental learning over time on multiple different training corpora, may have some advantages over non-incremental statistical CAMS which may not be updated after their initial training.

A neural network-based CAM, may, in some embodiments provide a CAM that is capable of being incrementally trained with relatively small subsets of coded patient encounters. The neural network model allows online or incremental learning. Neural networks are roughly modeled on the behavior of neurons in the human brain. Generally, neural networks consist of interconnected layers of nodes. The first layer, or the input layer, is provided with initial values (i.e. the features extracted from a note), then using the weights of the connections between the nodes (called edges), these values are fed through the network's hidden layers to the last output layer, whose nodes contain the final resulting values. This feeding of the values through the network is called a forward pass. So, given the initial values of the input nodes and the weights of the node connections, a forward pass through the network determines the output of the model. In the case of a CAM according to the description herein, such an output is a real number from 0 to 1 indicative of the confidence associated with a coded encounter.

Figure 1:
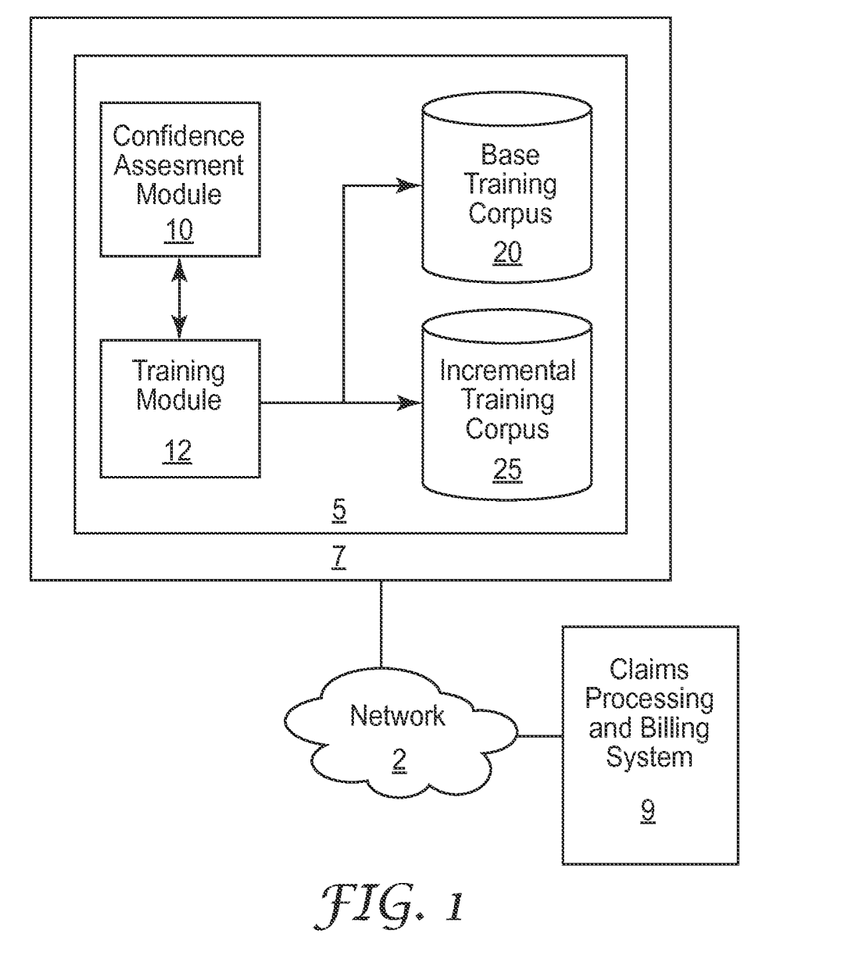
FIG. 1 is a system diagram showing functional components of a neural network-based confidence assessment module.

FIG. 1 is a system diagram showing neural network-based confidence assessment module 5, which may be implemented via software on a general purpose computing system 7. The computing system 7 includes memory and a processor for executing instructions. Neural network-based CAM 5 includes a number of functional modules, one embodiment of which is shown in FIG. 1. Confidence assessment module 10 (CAM 10) receives coded patient encounters and analyzes them using a neural network, and outputs a confidence value normalized to between 0 (low confidence, or likelihood, that the codes associated with the patient encounter are accurate) and 1 (high confidence, or likelihood, that the codes associated with the patient encounters are accurate.) Data describing the coded encounters come in via network 2, which may be a local area network, a wide area network (such as the Internet), or may be wired or wireless, as is known in the art. The coded encounters to be analyzed by the CAM may originate from any suitable source, but in one embodiment they originate from a healthcare organization's claims processing and/or billing system (shown in FIG. 1 as claims processing and billing system 9). The inner workings of the CAM 10, and how it implements a neural network, is further discussed below, in particular with respect to FIGS. 2 and 3.

Training module 12 is invoked to train the CAM 10, as needed. The need for such training is usually determined manually, either for initial setup, or because some drift in the CAM generated confidence values, as described earlier, has been seen. In some embodiments, training module 12 may be initiated to do the initial setup for an untrained CAM 10. Such may be the case for a healthcare provider installation where the provider has a number of validated coded encounters (as would result from human coded encounters), and wants to transition to a CAM-based approach. In such circumstance, a base training corpus 20 will have a number of coded encounters for the initial training of the CAM 10. The initial training corpus may be, e.g., in the range of 20,000 coded encounters. Training module 12 iterates through each coded encounter, invoking CAM 10 for each, then adjusts edge weights within the model to tune the model used by CAM 10 for assessments. In another embodiment, training module 12 may also iterate through multiple coded encounters in batches. There is essentially no difference between the initial training and later continued incremental training. Initially, all of the network edge weights are random values, and the initial training process adjusts them using the initial corpus to reduce error. Later, incremental trainings simply picks up where this initial training left off and continues to move the weights around to reduce error with respect to a new corpus. For an existing CAM that needs to be tuned or retrained, an incremental training corpus 25 would be used. It has the same basic structure as the base training corpus 20, in that it includes coded encounters, but usually it is smaller in total number of coded encounters. Also, the incremental training corpus 25 may only include coded encounters that are specific to a particular type of coded encounter that might be, e.g., new, or seen to be subject to drift. For example, a particular type of coded encounter related to a new procedure provided by the healthcare organization may be associated with an unacceptably high error rate associated with CAM assessments that result in direct-to-bill designations. The incremental training corpus 25 may be assembled, often manually, to include coded encounters associated with the new procedure, and provided to training module 12. For example, a few hundred coded encounters associated with the new procedure could be assembled in the incremental training corpus 25. Training module 12 may be invoked multiple times with different incremental training corpora 25. The manner by which the training module 12 works is further specified below.

Figure 2:
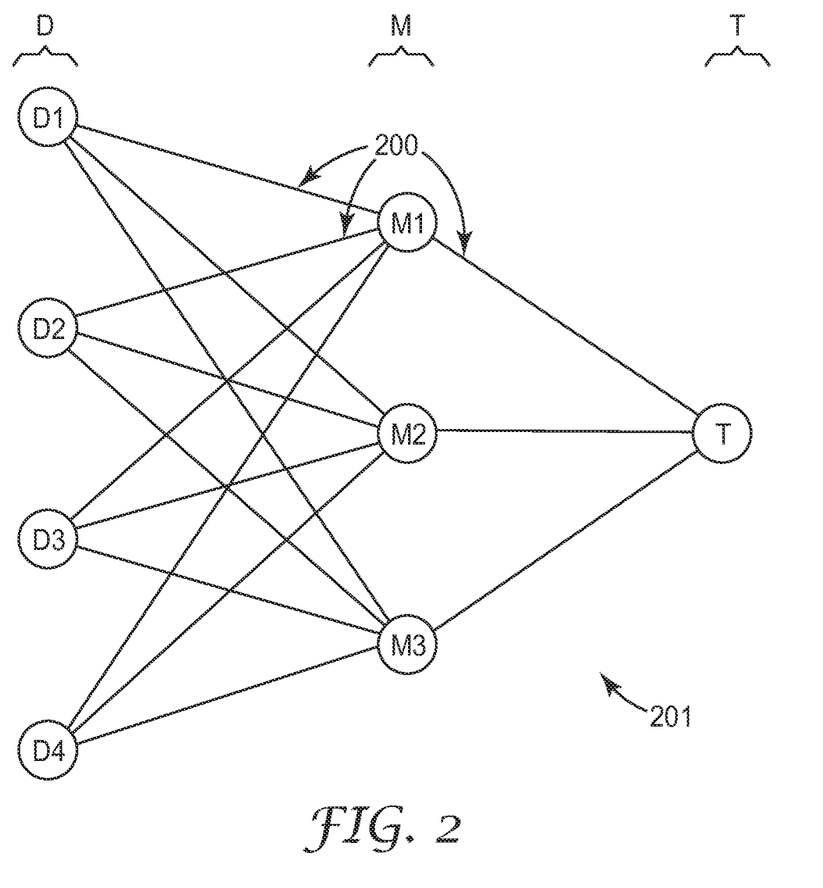
FIG. 2 is a simplified drawing of a neural network.

Turning now to FIG. 2, a simplified schematic of a neural network 201 as deployed in the CAM 10 is shown. The neural network model used with CAM 10 is a two layer network consisting of an input layer D with four nodes, a single hidden layer M, with three nodes, and an output layer T, as depicted in FIG. 1. The input nodes D are binary, that is, they are set with either the value 0 or 1. These values are derived from the analysis of features extracted from the patient's encounter-related health records while it is being processed by the NLP engine. In implementation, the number of input nodes D is variable depending on the attested features in a corpus and often numbers in the thousands.

That is, when determining the number of binary input nodes, all such features that exist in a training corpus (either the initial training corpus or the incremental training corpus) are examined and a single node is created for each attribute-value pair. For a particular note, an input node is set to 1 if that attribute-value pair appears in the note, and it is set to 0 if not. There is one additional bias input node, which always has the value 1. This type of node is commonly included in neural network models.

TABLE 1

| Attribute | Values |
|---|---|
| CPT Code | 74455, 74150, 37191, 37193, 72020 |
| ICD Code | 802.0, 656.63, 795.00, 788.20 |
| ICD Evidence Region | Clinical indication, impression . . . |
| ICD Evidence Location Modifier | Posterolateral proximal, surface, lower, superolateral . . . |
| Patient Sex | Female, male |

Given the attributes from Table 1 that may appear in a coded encounter and the attested values for those attributes in a particular corpus, each attribute-value pair is transformed into a binary feature, which will correspond to input node in the neural network. So, some binary node features may be "CPT Code:74455", "CPT Code:74150", "CPT Code:37191", "ICD Evidence Region:clinical indication", "ICD Evidence Region:impression", etc. If an encounter only had the CPT code 74150, then the binary node "CPT Code:74150" would be set to 1 while all other CPT code nodes like "CPT Code:74455" and "CPT Code:37191" would be set to 0.

There can be any arbitrary number of hidden nodes, layer M, which is set as a training parameter. Generally, the larger number of hidden nodes, the more types of complex relations and interactions can be modeled. However, if there are too many hidden nodes, this may result in overfitting which produces a poorly performing model. Similarly, there may also be any number of hidden node layers each with a different number of hidden nodes. The hidden layer also has an additional bias node. There is a single output node, T, which contains the confidence value of the note.

All of the network edges, the links between the nodes (such as edges 200), are associated with a weight value. The value of any node is computed by taking the sum of the product of the weights and their associated linking nodes, e.g., the edges that connect M1 to D1, D2, D3, and D4, as described in the following equation where a is the activation or value of a particular node, w is the weight of an edge, and x is the value of an input node.

$$a_j = \sum_{i=0}^{D} w_{ji} x_i$$

So, using this principle, the final value of the output node is calculated with the following equation where the superscripts (1) and (2) indicate the particular set of weights between two layers of nodes:

$$y(\vec{x}_n, w) = \sigma\left(\sum_{j=0}^{M} w_j^{(2)} \tanh\left(\sum_{i=0}^{D} w_{ji}^{(1)} x_i\right)\right)$$

This calculation defines a forward pass through the network. The activations of the nodes are transformed in this equation by the two common types of sigmoidal functions defined as follows, which constrain the values of the activations between −1 and 1 or 0 and 1:

$$\tanh(a) = \frac{e^{a_j} - e^{-a_j}}{e^{a_j} + e^{-a_j}}$$

$$\sigma(a) = \frac{1}{1 + e^{-a}}$$

The output node, T, should model the Bernoulli distribution which is particularly well suited for modeling the probability of binary options, such as whether a note is correctly or incorrectly coded. So, using the distribution, the probability that a particular encounter n is correctly, t=1, or incorrectly, t=0, coded given the binary feature vector (the input nodes) created for that encounter $\vec{x}_n$ and the weights of the neural network w, is found by the following equation:

$$p(t_n | \vec{x}_n, w) = y(\vec{x}_n, w)^{t_n} \{1 - y(\vec{x}_n, w)\}^{1-t_n}$$

This equation can be simplified and generalized to a whole set of encounters to find the probability that all the encounters have the correct target t value as follows:

$$p(t | \vec{x}, w) = \prod_{n=1}^{N} y_n^{t_n} \cdot (1 - y_n)^{(1-t_n)}$$

Figure 3:
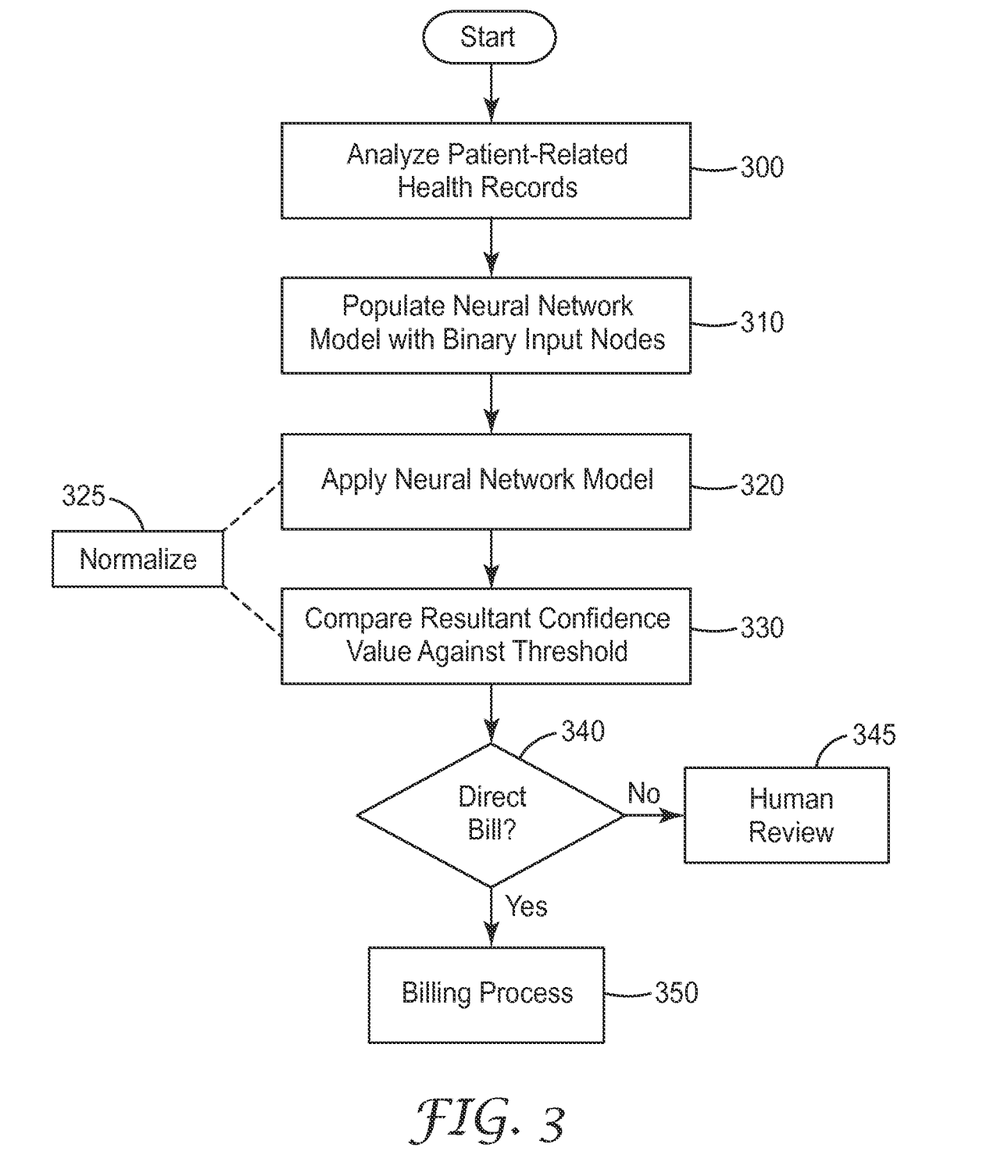
FIG. 3 is a flowchart showing the operation of a neural network confidence assessment module for evaluating coded encounters between a patient and a healthcare organization.

FIG. 3 shows a higher level schematic process flow of the above described process. Coded encounters are analyzed by, e.g., an NLP module to extract features (300). These features are then populated into a neural network model (310). The neural network model used in the embodiment described herein is a binary neural network, though other types of networks are possible. The binary neural network model is then applied as per the description above (320). A resultant confidence value, T, is then normalized to be between zero (no confidence) and 1 (high confidence). If necessary, the confidence value T may be normalized to another numeric scale (325). A confidence value is, in this way, associated with a coded patient encounter. Next, the T value is compared to a threshold established (330), usually, by the healthcare organization. The threshold defines the minimum confidence needed to send a coded patient encounter "direct-to-bill", thus not requiring any human review. This number might be, for example, 0.85. If the threshold value is exceeded by T, the coded encounter goes direct to bill (a "yes" at 340), resulting in initiation of the billing process at 350. If the confidence value T is not high enough and does not exceed the threshold, (no at 340), then the patient encounter is flagged for human review (345).

Figure 4:
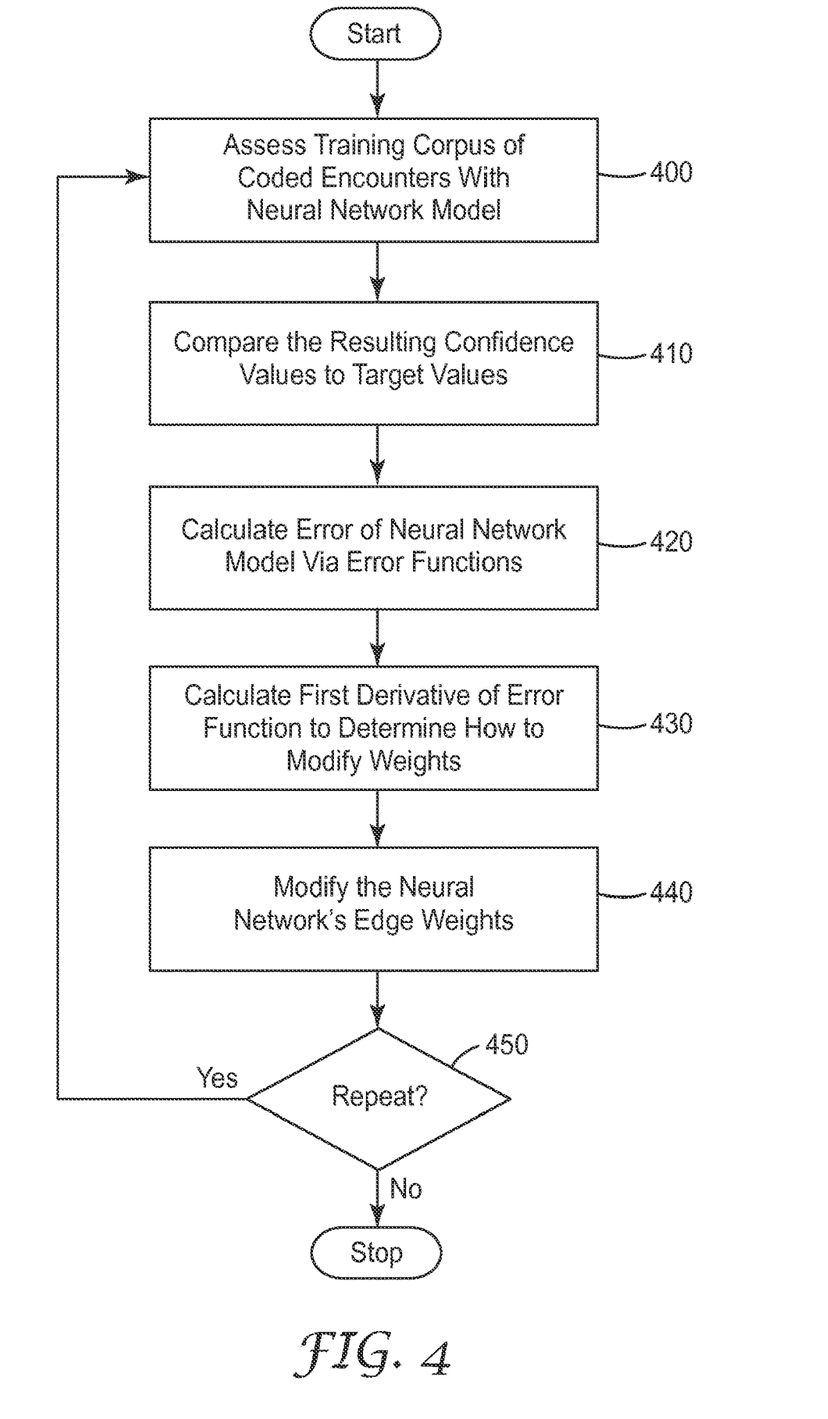
FIG. 4 is a flowchart showing how the neural network CAM may be incrementally trained with a corpus of training data.

Turning now to FIG. 4, a process flow is shown that illustrates a process by which the neural network-based CAM may be incrementally trained. A neural network-based CAM is trained and updated through a process known as backpropagation. First, a forward pass is done through the network using coded encounters in the incremental training corpus 25 (400). The resulting T value, or the confidence value, is compared to a target value (410). For example, the training corpus contains a mixture of human reviewed encounters, some with correct codes and others with incorrect ones. The CAM should assign relatively high confidence (a T value close to 1) to the correct encounters and a low confidence (a T value close to 0) to the incorrect encounters. An error function is then used to calculate the total error of the neural network model to assign correct confidence values (420). Determining the first derivative of the error function identifies the manner in which the edge weights should be modified to produce a T value closer to target (430). The neural network's edge weights (variables) are then adjusted accordingly (440), and a forward pass is performed again with the corpus, in an iterative manner, to determine if further adjustments to the edge weights are necessary ("yes" to repeat at 450).

In order to adjust the network weights so that the output more closely models the desired Bernoulli distribution given a training corpus of encounters and their target values, the error function (step 420) must be defined which indicates how the result is wrong with regard to the weights. In one embodiment, the error function is the negative log likelihood of the network, a standard method, formalized as follows:

$$E(w) = -\ln p(t \mid \bar{x}, w)$$
$$= -\sum_{n=1}^{N} \{t_n \ln y_n + (1 - t_n)\ln(1 - y_n)\}$$

So, by taking the partial derivative of this error function with respect to each layer of weights, it is possible to determine the direction and degree that the weights should be changed in order to reduce the error (step 430). First, to simplify the equations, the following variable is defined:

$$z_j = \tanh\left(\sum_{i=0}^{D} w_{ji}^{(1)} x_i\right)$$

Then, the derivatives of the error function with respect to each set of weights are:

$$\frac{\partial E}{\partial w_j^{(2)}} = (t_n - y_n) z_j$$

$$\frac{\partial E}{\partial w_j^{(2)}} = (t_n - y_n) w_j^{(2)} (1 - z_j^2) x_i$$

Although it is now known how the weights should be adjusted using the partial derivatives, they should be slowly changed as to not inadvertently make them worse. So, the weights will only be adjusted a portion of the partial derivatives' values, as is common practice. The global learning $\eta$ determines what portion of derivative is applied to all of the weights. Given the values of the weights at particular time $\tau$, the weights are updated as defined in the following formula:

$$w^{(\tau+1)} = w^{(\tau)} + \eta \nabla E(w^{(\tau)})$$

Generally, a set a training data (a collection of notes) is split into smaller batches which are individually fed through the network and then used for backpropagation to update the weights. So, to train on a whole dataset, there are multiple iterations of forward and backward passes through the network, which all together make one epoch of training. There are usually multiple epochs of training, and the learning rate is decreased with each epoch so that the weights converge on optimal values.

In addition to the global learning rate $\eta$, there are further learning rates associated with each weight which are each individually changed with each iteration through the network. This individual learning rate further modifies the partial derivative after the global learning rate. This type of learning, known as adaptive learning, is implemented by roughly following the existing RPROP algorithm. Generally, after each iteration of backpropagation, the partial derivative of the current iteration is compared to the derivative of the previous iteration. If the derivatives are both positive or both negative, indicating that the weight is consistently being changed in the same direction, then the individual learning rate is slightly increased. On the other hand, if the partial derivates have different signs, then it is likely that the weight is simply fluctuating back and forth, so the individual learning rate is decreased. Adaptive learning helps the whole training process converge on a result more quickly.

Generally the weights of a neural network are random values at the start of training. However, the weights may be seeded with the values of another previously trained model. This allows a new seeded model to begin training with already learned information. Such a seeded model not only trains faster because the weights are already close to their optimal values, but also allows the model to use inherited information from the seed model to access the confidence of some types of encounters which may have not been in its training corpus. The methods of seeding and updating models work in the same manner. In both cases, an existing network with previously learned weights is used for continued learning. In the case of seeding, there is a previously trained model which combines data across representative sites to create a general base CAM. This base CAM is then used as a seed for an individual site and updated with further training on data from that particular site. Starting with this general seed reduces the need for a large amount of site-specific data to train a CAM, which means that a new site does not have to wait as long to accumulate human-reviewed coded notes before getting a CAM.

When an existing CAM model is further trained on using new data, this is termed model updating. So, for instance, after a CAM has been trained for a particular site and put into production, at a later time, the CAM can be updated with new notes coded after the CAM was originally deployed. In this manner, if the types of notes or their content has changed, then the CAM is able to learn off of this new data and prevent any type of degraded performance that would have otherwise occurred.

The binary features chosen as input nodes for a CAM are based off of the attribute-value pairs existing in the first dataset that a new CAM is trained on, as previously described. Because seeding and updating models involves training a CAM with a different dataset at a later time, there may be new attribute-values pairs that are not already part of the CAM. If these input features are ignored, then this with prevent the CAM from learning new information. So, before seeding or updating a CAM, the existing set of binary input nodes must be expanded to include any new attribute-value pairs. This process requires modification of the existing neural network structure.

When adding a new input node to a network, its corresponding edges to the hidden layer must also be created. Because a hidden node's activation is calculated by the preceding connected nodes, this new node will affect its value.

However, if the weight of the new node is set to zero, then the node's activation is not affected by the new input node.

This is demonstrated mathematically by explicitly showing the calculation of a node's activation as follows:

$$a_j = \sum_{i=0}^{5} w_{ji} x_i$$
$$= w_{j1}x_1 + w_{j2}x_2 + w_{j3}x_3 + w_{j4}x_4 + 0 \cdot x_5$$
$$= w_{j1}x_1 + w_{j2}x_2 + w_{j3}x_3 + w_{j4}x_4$$

Thus, when new input nodes are added to an existing model when seeding or updating a model, then the corresponding weights of those new nodes are initially set to zero. Any subsequent training will then begin to change the weights to reduce the error of the model through backpropagation as previously described.

Similarly, if over the course of time and the addition of many new input nodes to a network, it may be determined that older input nodes are no longer used and only contribute to the size, and thus computational complexity, of the network. These unused nodes can be safely pruned from the network without affected its performance. That is, if an input node is never used, then its value will always be zero, thus its contribution to a node's activation value is always zero. So, its removal will not affect the activation calculations.

Using the neural network configuration described above which learns by backpropagation and the ability to expand the input nodes as needed for new datasets, these mechanisms are assembled to create a continued learning processes for CAMs which adapt to the changes in medical note content over time.

EXAMPLE

To illustrate the use of a neural network CAM with the capability for incremental learning, consider the following scenario: A healthcare provider site already has a neural network CAM in use. Then a new type of notes begins to be submitted to the CAM, the new notes associated with coding in new medical sub-specialties. The existing CAM has not seen notes in these sub-specialties, so it performs badly when evaluating them (a higher percentage of notes are flagged as errors by a quality control process, or fewer notes are being ranked with high enough confidence to be sent direct-to-bill) and thus requires further incremental training with small batches of notes over time to gradually learn to evaluate them.

To simulate this scenario, a large number of coded encounters were categorized by sub-specialty. A few types of sub-specialties were chosen, and their corresponding notes were separated out of the corpus to create two corpora from the same site with two different sets of sub-specialties. The number of notes for these corpora is shown in Table 2.

TABLE 2

Initial corpora sizes for incremental scenario.

| Total # Notes | 53781 |
|---|---|
| Total # Notes Corpus 1 | 39366 |
| Total # Notes Corpus 2 | 14415 |

These two corpora, split by sub-specialties, were then used to create six new transition corpora which represent the continual slow addition of coded encounters from new sub-specialties. So, the first transition corpus contains only coded encounters from sub-specialty corpus 1, representing the base case where only a few sub-specialties are handled. Then with each subsequent transition corpus, the proportion of coded encounters from sub-specialty corpus 2 is slowly increased and eventually remains constant. The number of coded encounters in each of these transition corpora is provided in Table 3. Each of these corpora represents a new set of coded encounters collected in sequence over time. It is on each of these transition corpora that incremental learning will be performed so that the CAM will learn to handle the coded encounters from the new sub-specialty.

First, before performing incremental learning, baseline scores were calculated for the case where a CAM was trained on the base corpus but then not incrementally updated with each subsequent transition corpus. I.e., the original base-trained CAM was simply applied to each transition corpus. The results of this baseline are provided in Table 4. For the purposes of testing, each transition corpus was further divided into a training and testing corpus. The training corpus is used to train new models and the test corpus is used to test the models such as this baseline. A testing corpus is 30% of a transition corpus.

TABLE 3

Size and composition of transition corpora.

| BASE CORPUS | |
|---|---|
| # Notes Corpus 1 | 17715 |
| # Notes Corpus 2 | 0 |
| TRANSITION CORPUS 1 | |
| # Notes Corpus 1 | 5210 |
| # Notes Corpus 2 | 801 |
| | 6011 |
| TRANSITION CORPUS 2 | |
| # Notes Corpus 1 | 4409 |
| # Notes Corpus 2 | 1602 |
| | 6011 |
| TRANSITION CORPUS 3 | |
| # Notes Corpus 1 | 3608 |
| # Notes Corpus 2 | 2403 |
| | 6011 |
| TRANSITION CORPUS 4 | |
| # Notes Corpus 1 | 2808 |
| # Notes Corpus 2 | 3203 |
| | 6011 |
| TRANSITION CORPUS 5 | |
| # Notes Corpus 1 | 2808 |
| # Notes Corpus 2 | 3203 |
| | 6011 |
| TRANSITION CORPUS 6 | |
| # Notes Corpus 1 | 2808 |
| # Notes Corpus 2 | 3203 |
| | 6011 |

TABLE 4

Baseline scores without incremental learning.

| Threshold | # Notes | % Capture | Primary ICD | CPT Recall | CPT Precision |
|---|---|---|---|---|---|
| BASE CORPUS | | | | | |
| 0.68 | 2867 | 53.94% | 91.98% | 98.18% | 98.89% |
| TRANSITION CORPUS 1 | | | | | |
| 0.77 | 750 | 41.60% | 94.40% | 97.91% | 98.55% |
| TRANSITION CORPUS 2 | | | | | |
| 0.9 | 389 | 21.58% | 97.17% | 98.25% | 98.49% |
| TRANSITION CORPUS 3 | | | | | |
| 0.8 | 494 | 27.40% | 91.90% | 98.81% | 99.22% |
| TRANSITION CORPUS 4 | | | | | |
| 0.97 | 95 | 5.27% | 93.68% | 100.00% | 100.00% |
| TRANSITION CORPUS 5 | | | | | |
| 0.94 | 179 | 9.93% | 94.41% | 97.96% | 98.46% |
| TRANSITION CORPUS 6 | | | | | |
| 0.83 | 379 | 21.02% | 92.61% | 97.96% | 98.47% |

TABLE 5

Scores after incremental learning.

| Threshold | # Notes | % Capture | Primary ICD | CPT Recall | CPT Precision |
|---|---|---|---|---|---|
| TRANSITION CORPUS 1 | | | | | |
| 0.77 | 828 | 45.92% | 93.36% | 97.93% | 98.38% |
| TRANSITION CORPUS 2 | | | | | |
| 0.89 | 433 | 24.02% | 97.23% | 98.10% | 97.89% |
| TRANSITION CORPUS 3 | | | | | |
| 0.87 | 499 | 27.68% | 91.98% | 98.28% | 98.62% |
| TRANSITION CORPUS 4 | | | | | |
| 0.91 | 482 | 26.73% | 93.98% | 97.95% | 98.57% |
| TRANSITION CORPUS 5 | | | | | |
| 0.74 | 481 | 26.68% | 92.10% | 97.85% | 98.03% |
| TRANSITION CORPUS 6 | | | | | |
| 0.78 | 648 | 35.94% | 91.98% | 98.05% | 98.41% |

A CAM is evaluated against a corpus by considering a few key metrics. As previously described, the neural network model used with CAMs produces the probability that a particular note is correct. A CAM is given a threshold, which is the lowest acceptable note confidence probability, and all notes with at least this probability are captured and sent direct-to-bill. The higher the capture rate, the better. However, it must be ensured that all of the captured notes are indeed correct. So, metrics related to ICD and CPT correctness are consulted to choose the best threshold. For each given threshold is it determined what percentage of the notes have the correct primary ICD code and what the CPT recall and precision are for those notes. Generally with higher thresholds, the ICD and CPT metrics become better while the capture rate decreases. So, the lowest threshold is chosen which maintains at least a 92% correct primary ICD score and at least 98% CPT recall and precision. These are the threshold and metrics which are provided in the evaluation tables.

By looking at the baseline scores in Table 4, we see that this static CAM model degrades in performance with each new transition corpus. The capture rate dramatically decreases. However, this can be avoided by using incremental learning, where the base model is updated by the training coded encounters for transition corpus 1, whose new model is then updated with the training coded encounters for transition corpus 2, and so on. This means that the CAM learns to identify new types of coded encounters over time. The results for incremental learning are shown in Table 5. Here it can be seen that the capture rate is higher than the baseline, particularly in the last few transition corpora. With further training on new corpora, the capture rate would continue to increase to its full potential level as the model better learns to identify the new types of notes.

The invention claimed is:

1. A computer-implemented method of incrementally training a confidence assessment module that calculates a confidence value indicative of the extent to which a code associated with a patient's encounter with a healthcare organization is proper, the computer-implemented method comprising:
   via a training module, automatically invoking the confidence assessment module to assess a training corpus comprised of a plurality of coded encounters, to produce resultant confidence values associated with each encounter;
   via the training module, automatically comparing the resultant confidence values to a target confidence value; and
   via the training module, automatically adjusting edge weight values within the confidence assessment module to produce resultant confidence values closer to the target confidence value;
   wherein the confidence assessment module is a neural network-based confidence assessment module comprising at least one layer of binary input nodes, one layer of intermediate nodes, and one layer of output nodes, and wherein nodes between layers are weighted with edge weight values, and wherein adjusting edge weight values comprises:
   applying an error function to variables within the confidence assessment module to determine an error of the resultant confidence value as compared with the target confidence value;
   calculating the derivative of the error function to determine how the edge weight values should be modified to decrease the error; and
   modifying the edge weight values.

2. The computer-implemented method of claim 1, wherein each of the plurality of coded encounters comprises documentation associated with a patient's encounter with a healthcare provider, and codes associated with that encounter.

3. The computer-implemented method of claim 1, wherein the output node comprises the confidence value.

4. The computer-implemented method of claim 1, further comprising:
   iteratively repeating the assessing, comparing, and adjusting step.

5. The computer-implemented method of claim 1, wherein the confidence value is indicative of the likelihood that the code associated with the patient's encounter with the healthcare organization is accurate.

6. The computer-implemented method of claim 1, wherein accurate means a human coder would have associated the same code with the encounter.

7. An incremental learning confidence assessment system that evaluates coded encounters between a patient and a healthcare organization and computes a confidence value indicative of the likelihood that codes associated with the coded encounters are proper, the system comprising:
- a confidence assessment module operative to receive coded encounters, the coded encounters comprising both (1) documentation associated with a patient's encounter with a healthcare organization, and (2) codes associated with that encounter, and using a neural network, compute the confidence value for the coded encounter; and,
- a training module that automatically invokes the confidence assessment module to evaluate a corpus of training notes, then automatically adjusts edge weight values within the confidence assessment module based on the evaluation;
- wherein the neural network comprises a binary neural network having a layer of binary input nodes, a layer of intermediate nodes, and an output node, the output node indicative of the confidence value; wherein nodes between layers are represented as edges, and edges are associated with an edge weight variable that defines the relative weight given to an edge;
- wherein the training module evaluates the resulting confidence values associated with the corpus of training notes against a target confidence value; and
- wherein the training module applies an error function to the edge weights to determine an error associated with at least some of the edge weights, and then calculates the derivatives of the error function to determine how the variables should be adjusted so the confidence values associated with the corpus are closer to the target confidence value.

8. The system of claim 7, wherein the training module causes the edge weights to be adjusted.

9. A computer-implemented method of calculating a confidence value indicative of the likelihood that a code associated with a patient's encounter with a healthcare organization is proper, the computer-implemented method comprising:
- analyzing, using a processor of the computer, patient-related healthcare records that relate to the patient's encounter with a healthcare organization, to extract attributes;
- representing at least some of the extracted attributes as binary input nodes associated with a neural network model that has an output node associated with the confidence value; and,
- applying the neural network model to the binary input nodes, to compute the confidence value associated with the output node;
- wherein the neural network model has a plurality of intermediate nodes and wherein weight values are associated with network edges that connect various nodes, and further comprising:
- comparing the confidence value associated with the output node to an expected value; and
- adjusting the weight values associated with the edges between the intermediate nodes automatically via a training module which assesses a training corpus comprised of a plurality of coded encounters such that the confidence value associated with the output node is within an acceptable deviance of the expected value;
- wherein the training module applies an error function to the weight values to determine an error associated with at least some of the weight values, and then calculates the derivatives of the error function to determine how the weight values should be adjusted so the confidence value associated with the patient-related healthcare records is closer to the expected value.

10. The computer-implemented method of claim 9, further comprising:
- comparing the confidence value to a threshold value, and based on the comparison, determining if the code and patient-related healthcare records should be further reviewed by a human reviewer.

11. The computer-implemented method of claim 10, further comprising:
- providing the patient-related health records to a human reviewer.

12. The computer-implemented method of claim 9, wherein the neural network model comprises a trained neural network model.

* * * * *